(12) United States Patent
Laszlo et al.

(10) Patent No.: US 11,576,601 B2
(45) Date of Patent: Feb. 14, 2023

(54) ARTIFACT IDENTIFICATION IN EEG MEASUREMENTS

(71) Applicant: X Development LLC, Mountain View, CA (US)

(72) Inventors: Sarah Ann Laszlo, Mountain View, CA (US); Nina Thigpen, Sunnyvale, CA (US); Vladimir Miskovic, Binghamton, NY (US); Yvonne Yip, San Francisco, CA (US)

(73) Assignee: X Development LLC, Mountain View, CA (US)

( * ) Notice: Subject to any disclaimer, the term of this patent is extended or adjusted under 35 U.S.C. 154(b) by 751 days.

(21) Appl. No.: 16/388,709

(22) Filed: Apr. 18, 2019

(65) Prior Publication Data
US 2020/0329990 A1   Oct. 22, 2020

(51) Int. Cl.
| | |
|---|---|
| A61B 5/00 | (2006.01) |
| A61B 5/374 | (2021.01) |
| A61B 5/291 | (2021.01) |
| G06N 3/08 | (2023.01) |
| A61B 5/316 | (2021.01) |
| G06N 20/00 | (2019.01) |

(52) U.S. Cl.
CPC .............. *A61B 5/291* (2021.01); *A61B 5/316* (2021.01); *A61B 5/6803* (2013.01); *A61B 5/7207* (2013.01); *A61B 5/7267* (2013.01); *G06N 3/08* (2013.01); *A61B 5/374* (2021.01); *A61B 5/6814* (2013.01); *A61B 5/7221* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 7,684,856 B2 | 3/2010 | Virtanen et al. | |
| 8,364,255 B2 | 1/2013 | Isenhart et al. | |
| 2002/0183644 A1* | 12/2002 | Levendowski | A61B 5/7264 600/544 |
| 2004/0260169 A1* | 12/2004 | Sternnickel | A61B 5/726 600/409 |

(Continued)

FOREIGN PATENT DOCUMENTS

WO    WO-2017143319 A1 *   8/2017   ............. A61B 5/291

*Primary Examiner* — Etsub D Berhanu
(74) *Attorney, Agent, or Firm* — Fish & Richardson P.C.

(57) ABSTRACT

Methods, systems, and computer programs encoded on a computer storage medium, for improving EEG measurements by identifying artifacts present in EEG measurements and providing a real-time indication to a user of likely artifacts in EEG measurements are described. EEG measurements of a patient can be obtained by placing a wearable device or EEG cap on a patient's head. Sensors in the cap provide EEG data to a computing device that processes the data to identify one or more artifacts in the EEG data. The artifacts can be identified by conducting one or more operations of determining the signal to noise ratio of the line noise, calculating mutual information between sensor pairs, and applying the p-welch method. Based on the types of artifacts identified, the computing device can output an indicator that provides feedback to the technician performing an EEG test to make adjustments to the test setup.

22 Claims, 7 Drawing Sheets

(56) References Cited

U.S. PATENT DOCUMENTS

| | | | |
|---|---|---|---|
| 2006/0235321 A1* | 10/2006 | Simske | A61B 5/341 600/512 |
| 2007/0265537 A1* | 11/2007 | Lee | A61B 5/333 600/509 |
| 2008/0077039 A1* | 3/2008 | Donnett | A61B 5/0006 600/544 |
| 2009/0062680 A1 | 3/2009 | Sandford | |
| 2010/0249551 A1* | 9/2010 | Miller | A61B 5/6843 600/323 |
| 2013/0138356 A1 | 5/2013 | Nierenberg et al. | |
| 2014/0148723 A1* | 5/2014 | Nierenberg | A61B 5/316 600/544 |

* cited by examiner

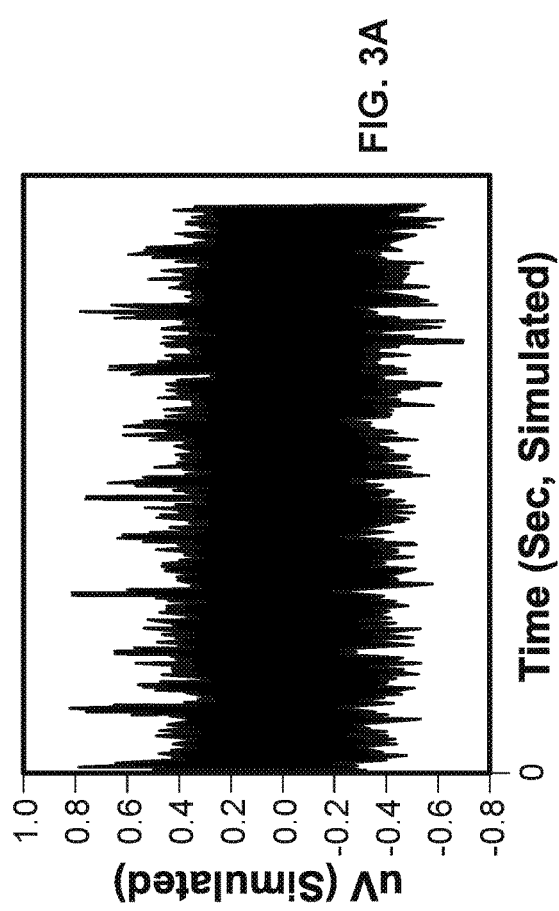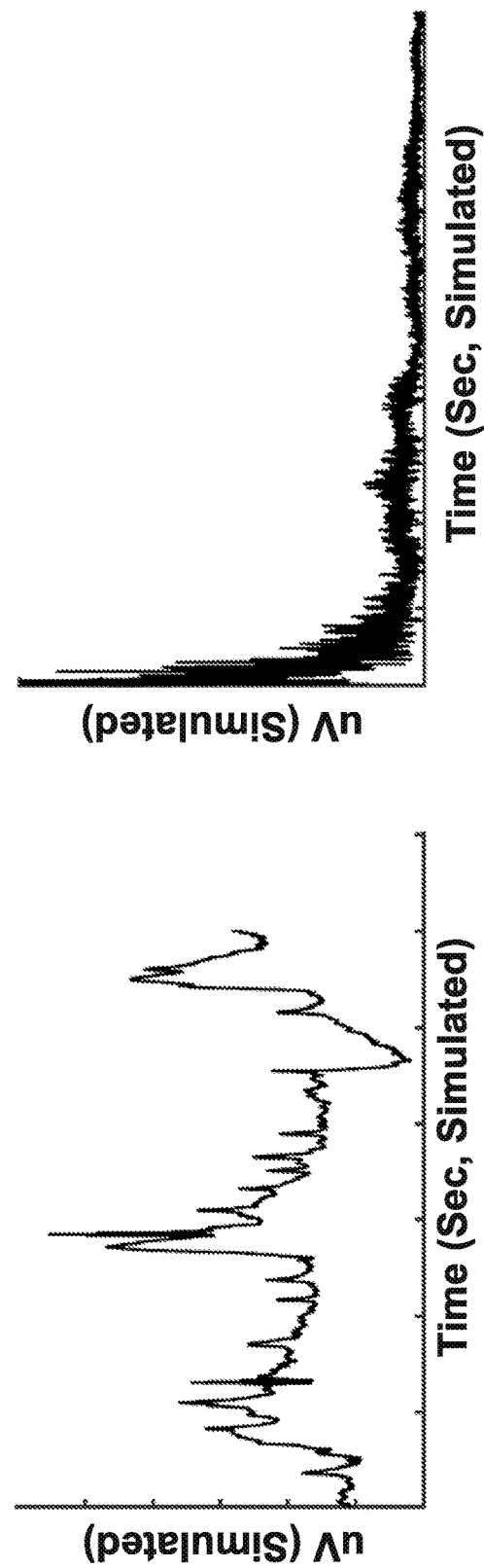
FIG. 3A
FIG. 3B
FIG. 3C

ARTIFACT IDENTIFICATION IN EEG MEASUREMENTS

FIELD

This disclosure generally relates to EEG measurements.

BACKGROUND

Electrical signals of the brain can be measured using brainwave measurement systems such as electroencephalogram (EEG) machines. The quality of brain signal data obtained by EEG systems varies widely and can be susceptible to noise and inaccuracies.

SUMMARY

This specification describes systems, methods, devices, and other implementations for improving EEG measurements by identifying artifacts in EEG measurements and providing a real-time indication of likely artifacts that are contributing noise to EEG measurements to a user. The indication can also be accompanied with recommendations on how to adjust the EEG measurement setup so that improved EEG measurements can be obtained.

EEG measurements of a patient can be obtained by placing a wearable device or EEG cap on a patient's head. Sensors in the wearable device provide EEG data to a computing device that processes the data to identify one or more artifacts in the EEG data. In some examples, the artifacts are identified by conducting one or more operations of determining the signal to noise ratio of line noise, calculating mutual information between sensor pairs, and applying the p-welch method. Based on the types of artifacts identified, the computing device can output an indicator that provides feedback to the technician performing an EEG test to make adjustments to the test setup. For instance, the computing device can indicate to the technician whether errors in the obtained EEG data are due to environmental noise, patient noise (e.g., patient movement), and/or poor sensor contact with a patient's skull. The technician may then take corrective action and obtain new EEG measurements so that improved and more reliable EEG data can be obtained for patients.

In general, innovative aspects of the subject matter described in this specification can be embodied in a computer-implemented method that include one or more operations executed by one or more processors. The operations include obtaining brainwave data from a wearable device comprising brainwave sensors. A determination that an artifact is likely present in the brainwave data is made by performing one or more of line noise signal to noise ratio (SNR)-based determination, a mutual information determination, and a P-welch method. An output message template corresponding to the artifact that is likely present in the brainwave data is obtained. An output indicative of a quality of the brainwave data is generated based on the output message template corresponding to the artifact that is likely present in the brainwave data.

In some implementations, the operation of determining that an artifact is likely present in the brainwave data by performing the line noise signal to noise ratio (SNR)-based determination includes the operations of: generating frequency brainwave data from the brainwave data obtained from the brainwave sensor; generating a power spectrum of the frequency brainwave data; determining a signal to noise ratio across the power spectrum; and determining a signal to noise ratio peak at a predetermined frequency associated with one or more of a utility line frequency, power line frequency, and an alternating current frequency.

In some implementations, the operation of determining that an artifact is likely present in the brainwave data by performing the mutual information determination includes the operations of: determining a mutual information value between two sensors of the brainwave sensors; and determining that the mutual information value is greater than or equal to a threshold value.

In some implementations, the operation of determining that an artifact is likely present in the brainwave data by performing the p-welch method includes the operations of: generating frequency brainwave data from the brainwave data obtained from the brainwave sensor; generating a power spectrum of the frequency brainwave data; applying a first degree polynomial to a logged representation of the power spectrum; and determining that a slope of the first degree polynomial or shape of the logged representation of the power spectrum corresponds to a slope or shape associated with an artifact.

In some implementations, the operation of determining that an artifact is likely present in the brainwave data includes performing two or more of the line noise signal to noise ratio (SNR)-based determination, the mutual information-based determination, and the P-welch method.

In some implementations, the operations of the computer-implemented method further include identifying one or more of a participant-based artifact, environmental artifact, and a cap-based artifact in the brainwave data in response to determining that an artifact is likely present in the brainwave data.

In some implementations, the operation of identifying one or more of a participant-based artifact, environmental artifact, and a cap-based artifact in the brainwave data in response to determining that an artifact is likely present in the brainwave data includes the operations of: determining an outcome of performing the one or more of line noise signal to noise ratio (SNR)-based determination, a mutual information determination, and a p-welch method; obtaining artifact models from an artifact database; comparing the outcome to the artifact models; determining that a similarity between the outcome and one of the artifact models satisfies a similarity threshold; and determining that the brainwave data includes one or more of a participant-based artifact, environmental artifact, and a cap-based artifact in response to determining that the similarity threshold is satisfied.

In some implementations, the artifact models are generated using a neural network and training data.

In some implementations, the operation of obtaining the output message template corresponding to the artifact that is likely present in the brainwave data includes transmitting and receiving operations. In particular, a request for an output message template corresponding to the one or more of a participant-based artifact, environmental artifact, and a cap-based artifact identified in the brainwave data is transmitted to a mapping table database, and the output message template is received from the mapping table database.

In some implementations, the output generated based on the output message template includes a recommendation for eliminating the one or more of a participant-based artifact, environmental artifact, and a cap-based artifact identified in the brainwave data.

According to some implementations, a system includes a wearable device and a data processor. The wearable device includes brainwave sensors that are configured to obtained brainwave data. The data processor is communicably coupled to the brainwave sensors. The data processor is configured to determine that an artifact is likely present in the brainwave data by performing one or more of line noise signal to noise ratio (SNR)-based determination, a mutual information determination, and a p-welch method. The data processor is configured to obtain an output message template corresponding to the artifact that is likely present in the brainwave data, and generate an output indicative of a quality of the brainwave data based on the output message template corresponding to the artifact that is likely present in the brainwave data.

According to some implementations, a non-transitory computer-readable storage medium includes instructions, which when executed by one or more computers, cause the one or more computers to execute operations. The operations include: obtaining brainwave data from a wearable device comprising brainwave sensors and determining that an artifact is likely present in the brainwave data by performing one or more of line noise signal to noise ratio (SNR)-based determination, a mutual information determination, and a p-welch method. The operations also include obtaining an output message template corresponding to the artifact that is likely present in the brainwave data, and generating an output indicative of a quality of the brainwave data based on the output message template corresponding to the artifact that is likely present in the brainwave data.

Other aspects include corresponding methods, systems, apparatus, computer-readable storage media, and computer programs configured to implement the operations of the above-noted methods.

The details of one or more implementations of the subject matter of this disclosure are set forth in the accompanying drawings and the description below. Other features, aspects, and advantages of the subject matter will become apparent from the description, the drawings, and the claims.

DESCRIPTION OF DRAWINGS

FIGS. 3A-3C depict example brainwave data signals according to implementations of the present disclosure.

Like reference numbers and designations in the various drawings indicate like elements.

DETAILED DESCRIPTION

Figure 1:
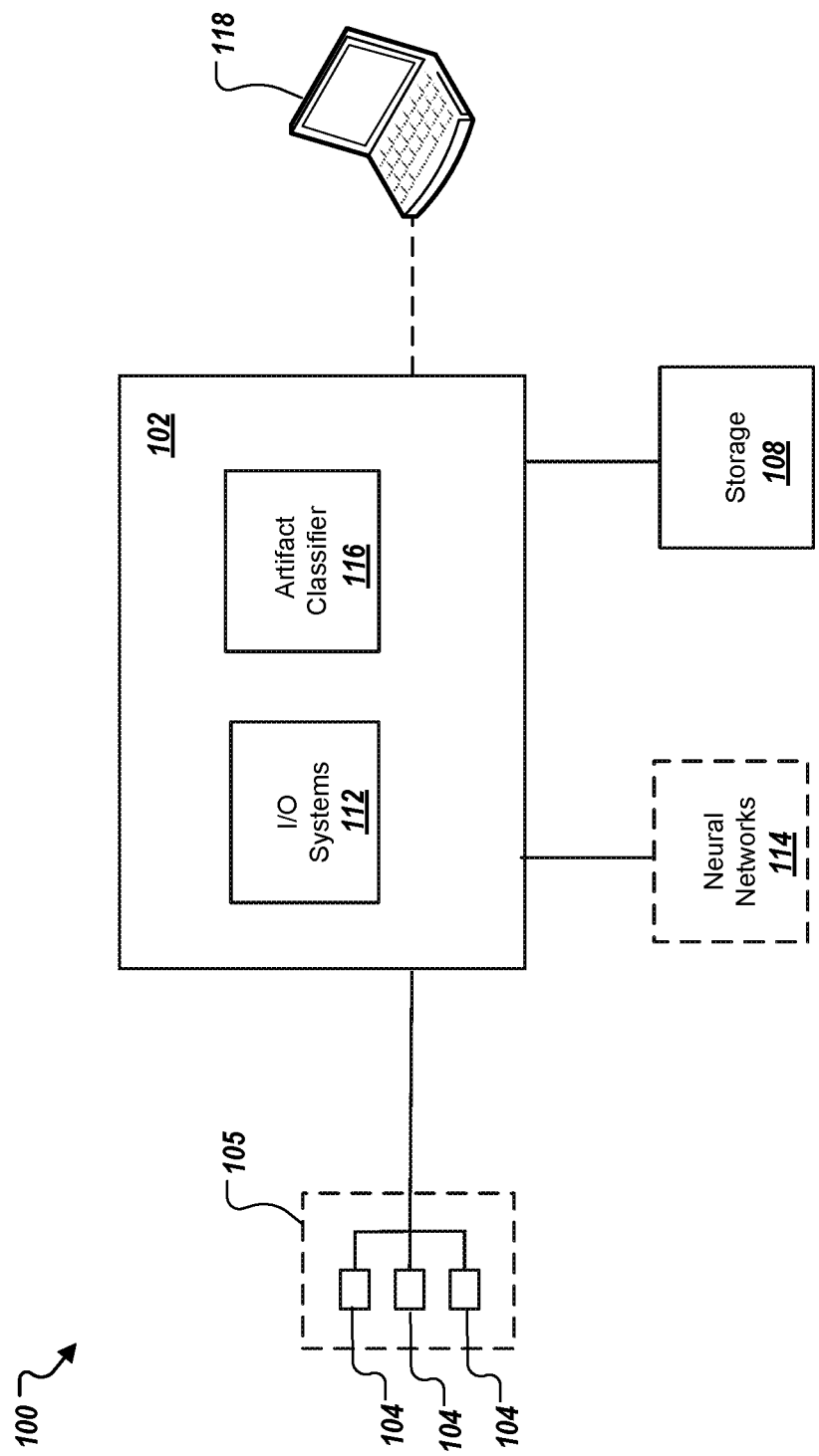
FIG. 1 depicts block diagram of an example system for obtaining brainwave data in accordance with implementations of the present disclosure.

EEG systems provide insight into the neural activity of a patient's mental health. In particular, wave patterns recorded through EEG systems can provide characteristic data of mental states such as anxiety, stress, excitement, or depression.

However, obtaining reliable EEG data is difficult. Technicians or users generally have to be trained for several years to use an EEG system to collect, analyze, and interpret EEG data. Furthermore, collected EEG data is susceptible to errors arising from various sources such as patient noise, environmental noise, or cap noise.

Patient noise includes noise that is generated as a result of patient movement, such as blinking, moving body parts, grinding teeth, or sniffing. Environmental noise includes noise that is generated by interferences in the surroundings of a patient. Examples of environmental noise include interferences due to electromagnetic signals such as a cell phone signal, electrical appliances such as microwaves or refrigerators being plugged into a socket and drawing a certain amount of power, or a powerful magnet being placed near a patient. Cap noise can be generated when an EEG cap placed on a patient's head has one or more sensors that have poor contact with a patient's scalp. In this disclosure, a patient refers to the person whose brainwave or EEG data is being obtained.

Identifying and removing the above-noted sources of errors from EEG data has been difficult. Furthermore, no real time mechanism is widely available to compensate for these errors or to provide guidance to technicians to modify the test setup (e.g., to adjust the placement of the cap on a patient for better contact) to obtain better EEG data. As a result, technicians often realize that the EEG data obtained for a patient contained several errors after the data is processed and analyzed, which could be hours or days later. Consequently, tests have to be repeated with the hope that new EEG data does not contain the same errors. Such a scenario is undesirable for technicians as well as patients due to the inefficiencies and delays in obtaining accurate EEG data.

Disclosure in this specification describes several advantages that provide a solution to the above-noted problems. As described in further detail below, measurements obtained from an EEG system can be processed to identify artifacts. The artifacts can be identified using one or more of a signal to noise ratio (SNR)-based method for detecting line noise, a mutual information-based method, and a P-welch method. The likely source of error is determined based on the identified artifacts. A real-time output is then generated that provides guidance to a technician on whether the measurements are satisfactory or if adjustments should be made based on the likely source of error. In some cases, the output can also include a recommendation for action to improve the EEG measurements.

To identify the artifacts, machine learning techniques and neural networks can be used in conjunction with training data to create models for the artifacts, e.g., patient noise, environmental noise, and cap noise. The training datasets can include datasets with known artifacts. For example, numerous timed samples of EEG data affected with noise from surrounding electrical appliances, such as a refrigerator or microwave, can be obtained and contrasted with timed samples of clean EEG data unaffected by environmental noise or other types of artifacts to determine how EEG datasets with environmental noise arising from appliances can be modeled. Other datasets can similarly be used to create models for other artifacts.

Hereinafter, example implementations of the methods and systems for obtaining improved EEG data by minimizing the effect of artifacts are described.

FIG. 1 depicts a block diagram of an example system 100 for obtaining EEG data in accordance with implementations of the present disclosure. The system includes a brainwave data processor 102 which is configured to communicate with brainwave sensors 104 in a brainwave sensor system 105 such as an EEG cap. The data processor 102 can be implemented as a hardware or a software module. For example, the data processor 102 can be a hardware or software module that is incorporated into a computing system such as a brainwave monitoring system, a desktop or laptop computer, or a wearable device. The data processor 102 is configured to receive brainwave data of a patient from the brainwave sensors 104. In some implementations, additional sensors can be used to obtain data related to other physiological actions of the patient such as body movements.

Brainwave sensors 104 are configured to obtain raw EEG data in the form of brainwave data. User physiological actions such as muscular movements (e.g., in the face, head, and eyes), heartbeats, and respiration can create noise in the brainwave signals received by brainwave sensors 104. This noise can be generated due to one or more electrical signals of a person's body (e.g., nervous system impulses to control muscle movements) that interfere with the brainwave data, other brain signals for controlling such physiological actions, or both.

In general, various suitable types of sensors can be used as brainwave sensors 104. In some implementations, the brainwave sensors 104 can be one or more individual electrodes (e.g., multiple EEG electrodes) that are connected to the data processor 102 by wired or wireless connections. The brainwave sensors 104 can be part of a brainwave sensor system 105, such as an EEG cap, that is in communication with the data processor 102. A brainwave sensor system 105 can include multiple individual brainwave sensors 104 and computer hardware (e.g., processors and memory) to receive, process, and/or display data received from the brainwave sensors 104. Example brainwave sensor systems 105 can include, but are not limited to, EEG systems, a wearable brainwave detection device (e.g., as described below in reference to FIG. 2 below), a magnetoencephalography (MEG) system, and an Event-Related Optical Signal (EROS) system, sometimes also referred to as "Fast N IRS" (Near Infrared spectroscopy).

Figure 2:
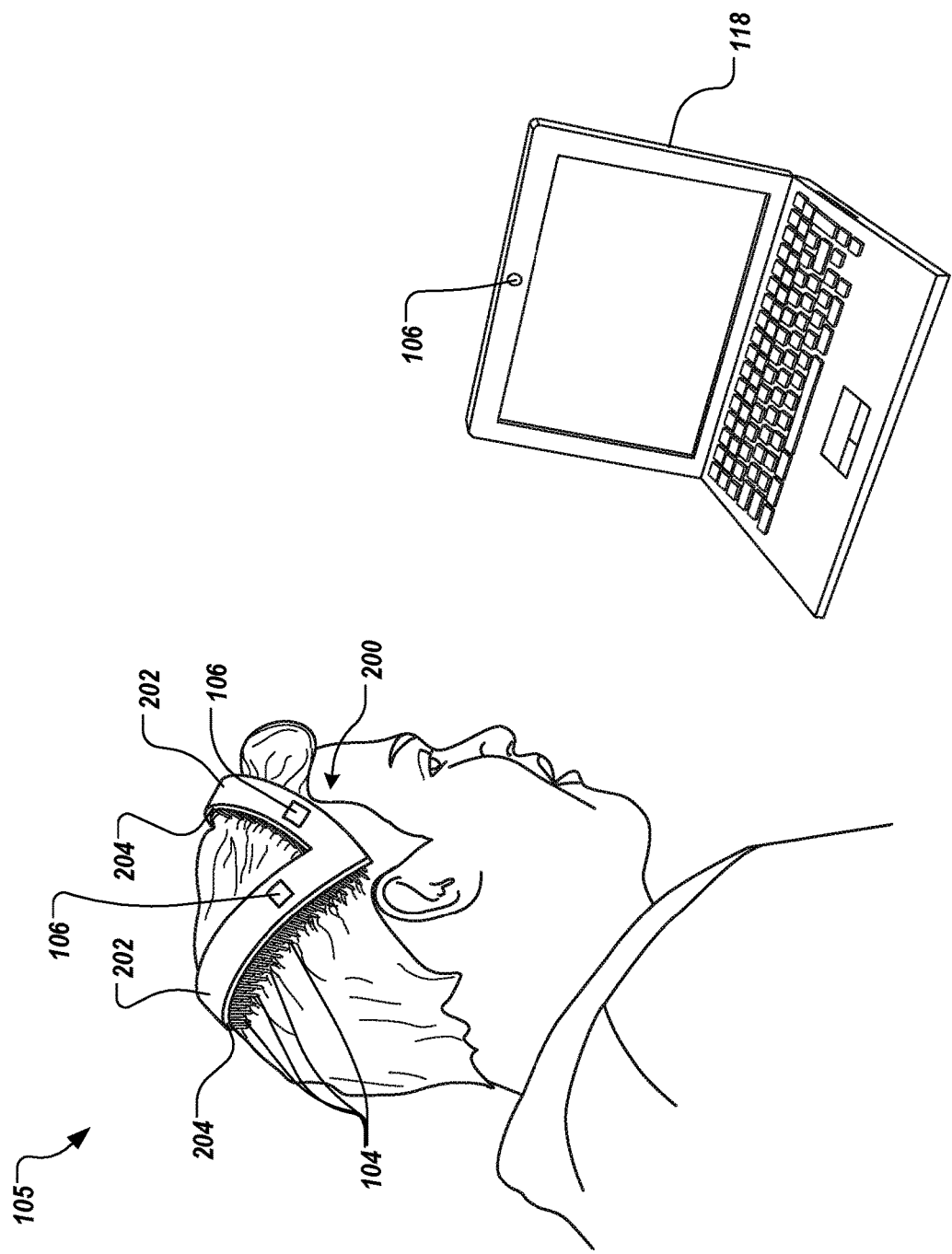
FIG. 2 depicts an example of a wearable device used to obtain brainwave data according to implementations of the present disclosure.

FIG. 2 depicts an example brainwave sensor system 105. In some implementations, the brainwave sensor system 105 may be a wearable device 200 which includes a pair of bands 202 that fit over a patient's head. The wearable device 200 includes one band which fits over the front of a patient's head and the other band 202 which fits over the back of a patient's head, securing the device 200 sufficiently to the patient during operation. The bands 202 include a plurality of brainwave sensors 104. The sensors 104 can be, for example, electrodes configured to sense the patient's brainwaves through the skin. For example, the electrodes can be non-invasive and configured to contact the patient's scalp and sense the patient's brainwaves through the scalp. In some implementations, the electrodes can be secured to the patient's scalp by an adhesive.

The sensors 104 are distributed across the rear side 204 of each band 202 or the side facing the patient. In some examples, the sensors 104 can be distributed across the bands 202 to form a comb-like structure. For example, the sensors 104 can be narrow pins distributed across the bands 202 such that a patient can slide the bands 202 over the patient's head allowing the sensors 104 to slide through the patient's hair, like a comb, and contact the patient's scalp. Furthermore, the sensors 104 distributed on the bands 202 can enable the device 200 to be retained in place on the patient's head by the patient's hair. In some implementations, the sensors 104 are retractable. For example, the sensors 104 can be retracted into the body of the bands 202.

The wearable device 200 is in communication with a computing device 118, e.g., a laptop, tablet computer, desktop computer, smartphone, or brainwave data processing system. For example, the data processor 102 can be implemented as a software application on a computing device 118. The wearable device 200 communicates brainwave data received from the sensors 104 to the computing device 118. In some implementations, the data processor 102 can be implemented on the wearable device 200. In such implementations, the device 200 can communicate brainwave data to the computing device 118 for use by other applications on the computing device, e.g., medical applications, brainwave monitoring applications, research applications.

A simulated example of brainwave data that can be received from one brainwave sensor is shown in FIG. 3A. The signal in FIG. 3A represents an aggregate electrical signal that can include multiple signal patterns related to environmental noise, patient noise, environmental noise, and/or cap noise and brainwave patterns related to mental activities of the patient. Examples of patient actions that give rise to participant noise include, but are not limited to, head movements, movements of facial muscles, a pulse rate (e.g., heartbeat), eye movements, respiration, or a combination thereof.

As described in more detail below, the EEG system may generate one or more recommendations for the technician to improve the EEG data shown in FIG. 3A. The time domain and frequency domain signals shown in FIGS. 3B and 3C are obtained after a technician takes one or more steps recommended by the EEG system to remove the sources of noise, e.g., by asking the patient to stop making head or facial movements or rechecking (and adjusting as needed) contact of sensors in the wearable brainwave detection device with a patient's scalp. The signal in FIG. 3A can be contrasted with the signal shown in FIG. 3B, which depicts the brainwave pattern without the participant noise i.e., a clean EEG signal associated with the patient.

Referring back to FIG. 1, the data processor 102 can include or be coupled to I/O Systems 112, one or more neural networks 114, an artifact classifier 116, and storage 108, each of which can be implemented using a combination of hardware and software. Storage 108 can be located remotely from the data processor 102 or integrated with the device on which the data processor 102 is implemented, e.g., in a computer or server.

The I/O Systems 112 can include input and output units that are configured to receive data from other systems and components and provide data to other systems and devices. For example, I/O Systems 112 can include input devices such as a keyboard, a pointing device, a mouse, a stylus, and/or a touch sensitive panel, e.g., a touch pad or a touch screen. The input devices may be any suitable device capable of receiving information through any type of medium, e.g., microphones for audio data, optical cameras for video data, etc. Output devices may include displays, screens, speakers, and, in general, any device that can output digital data through various media.

I/O Systems 112 can also include a transceiver that includes a transmitter and a receiver, and can be utilized to communicate with a server. The transceiver can include amplifiers, modulators, demodulators, antennas, and various other components. The transceiver can transfer or route data between the processor and other systems and components. For example, the transceiver can include a communication interface configured to transmit data between the data processor 102 and other systems and components such as storage 108, brainwave sensors 104, and/or computing devices 118.

The I/O Systems 112 can include a wired communication (e.g., USB, Ethernet) or wireless I/O Systems (e.g., Bluetooth, ZigBee, WiFi). The I/O Systems 112 can be used to communicate directly or indirectly, e.g., through a network, with other remote computing devices 118 such as, e.g., a laptop, a tablet computer, a smartphone, etc.

Storage 108 can be implemented using various types of memory systems as described below with reference to FIG. 7. For example, storage 108 can be implemented as one or more mass storage devices, for example, magnetic, magneto optical disks, optical disks, EPROM, EEPROM, flash memory devices, and can be implemented as internal hard disks, removable disks, magneto optical disks, CD ROM, or DVD-ROM disks for storing data.

In some implementations, storage 108 can store computer programs and code used by the processor 102 for executing operations such as code that facilitates receiving brainwave data and extracting artifacts for from the received brainwave data.

In some implementations, the storage 108 can also store one or more training data sets. The data sets can include data associated signal characteristics/EEG data representative of different types of artifacts as well as data sets that include signal characteristics/EEG data lacking artifacts. For example, storage 108 can store a participant noise dataset, an environmental noise dataset, a cap noise data set, and a clean EEG dataset. Training data can be updated periodically or each time measurements are obtained using brainwave sensor system 105. In the latter case, newly obtained measurements can be processed as described below to identify artifacts present in the obtained EEG data. The obtained measurements or data derived from the obtained measurements can then be added to a dataset of the artifact identified as being present in the obtained measurements.

Figure 4A:
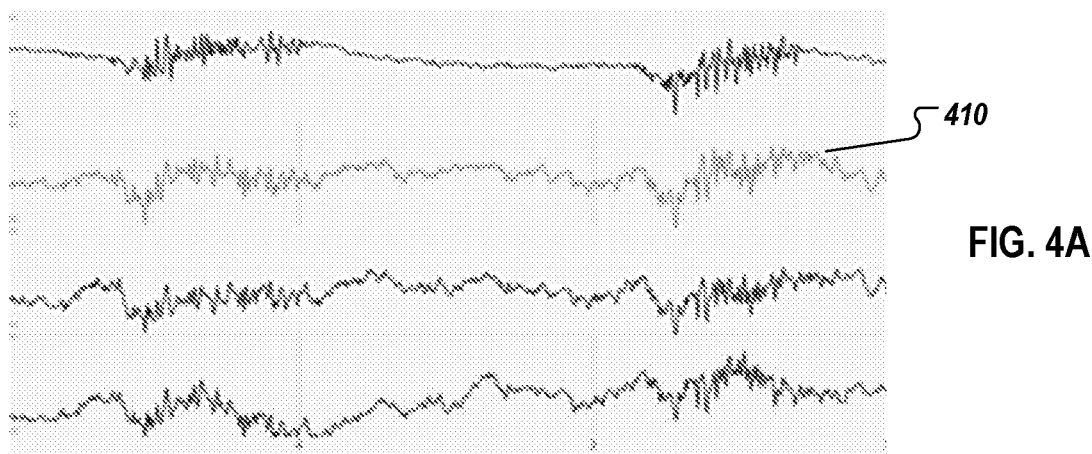
FIGS. 4A-4C depicts examples of training data used for modeling artifacts according to implementations of the present disclosure.
Figure 4B:
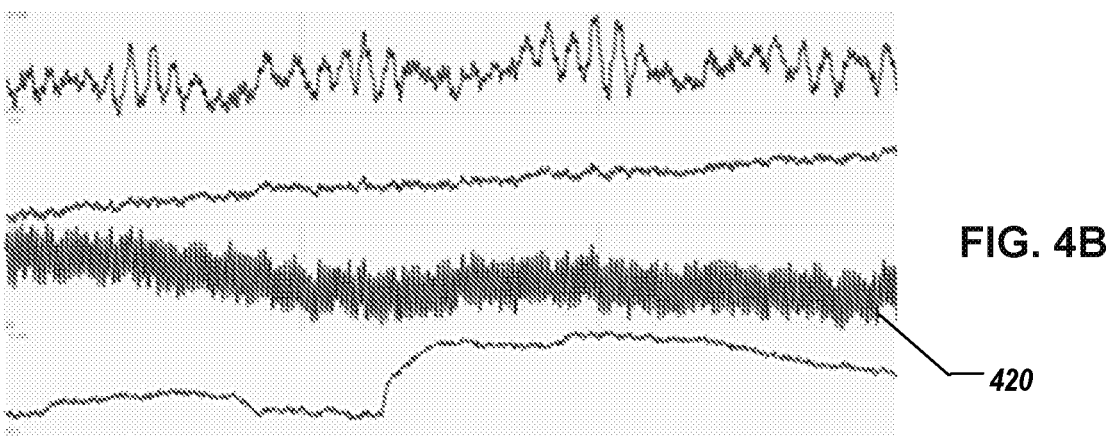
Figure 4C:
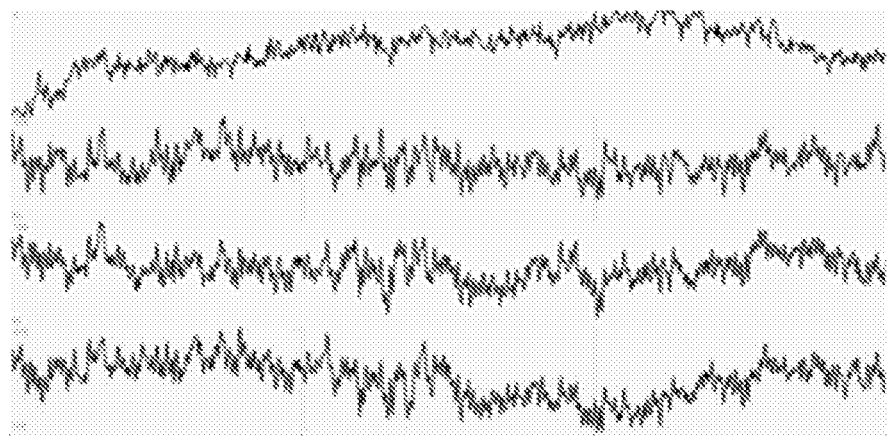

Examples of training data are depicted in FIGS. 4A-4C. FIGS. 4A-4C show brainwave data obtained by 4 different sensors in brainwave sensor system. For example, the periodic high frequency bursts shown in FIG. 4A are examples of participant noise dataset. In the illustrated example, FIG. 4A depicts a common artifact originating from the bilateral masseters, which occurs when a patient is grinding teeth together. Thus, line 410 can be selected as training data for an artifact associated with a participant noise dataset, and more particularly, with a patient grinding teeth.

FIG. 4B depicts an example in which each of the sensors picks up different data. In particular, signal pattern 420 is corrupted with a 60 Hz noise artifact. Thus, signal pattern 420 can be selected as training data for an artifact associated with an environmental noise. FIG. 4C depicts an example in which the recorded signals across all electrodes are similar, indicating that all the electrodes are picking up some artifact. Similar signals across all electrodes can be attributed to EEG electrodes being misplaced, e.g., if an electrode is sitting on top a patient's hair and is not in direct contact with the patient's scalp. Thus, the mutual information between sensor pairs can be selected as training data for an artifact associated with a cap noise data set, and more particularly, with an electrode being misplaced.

While this specification describes artifacts such as participant noise, environmental noise, and cap noise, the methods and systems described herein are not limited to these three artifacts. For example, datasets for other types of artifacts can be stored in storage 108 and used by processor 102 for training purposes or to identify corresponding artifacts in EEG data obtained from a patient. In addition, datasets for training data can be of varying length. For example, the datasets may have signal data spanning a period of time, e.g., 2 seconds, 5 seconds, 10 seconds, 30 seconds, or a minute.

In some implementations, storage 108 can also include a mapping table. The mapping table can include one or more records of a database and arrange the records using data fields. For example, in some implementations, a particular data field includes information on various artifact types and another data field that includes records associated with output message templates. The mapping table can correlate one or more output message templates listed in an output message template data field to a type of artifact listed in an artifact data field. For instance, the mapping table stores data that maps each of a participant noise artifact, an environmental noise artifact, and a cap noise artifact to an output message template.

As an example, an output message template for an environmental noise artifact can include instructions for the technician to check the environment for interfering devices such as cell phones or microwaves. An output message template for a participant noise artifact can include instructions for the technician to ask the patient to reduce moving, grinding teeth, or breathing less heavily. An output message template for a cap noise artifact can include instructions for the technician to check the contact between an electrode and the scalp of a patient.

In some implementations, processor 102 can transmit a request for an output message template corresponding to a particular type of artifact, e.g., a participant-based artifact, environmental artifact, and a cap-based artifact, to the mapping table. The mapping table can process the request by identifying the output message template mapped to the particular type of artifact in the mapping table, and transmit the mapped output message template In some implementations, output message templates can be customized for certain types of movements and can be correlated to particular artifacts in the mapping table. For instance, an output message template mapped to an artifact associated with the specific type of body movement (e.g., movement of the arm or grinding of teeth) can include instructions for the technician to request the patient to stop moving the part of the body (e.g., arm, teeth) causing the artifact to be present in the EEG data.

In another example, an output message template mapped to cap noise artifacts can include instructions for the technician to check the EEG cap and make sure the electrodes in the EEG cap have good contact with the patient's scalp. In some cases, if EEG data is obtained from a particular sensor, the output message template can include a data field that can be filled with an identification of the particular sensor so that a message that is output includes an identification of the particular sensor that does not have good contact with the patient's scalp.

In some implementations, the one or more neural networks 114 can use the training data stored in storage 108 and machine learning models to train the artifact classifier 116 to identify artifacts present in brainwave data obtained from a patient. For example, the one or more neural networks 114 can include a machine learning model that has been trained to receive model inputs, e.g., artifact-free signal patterns, and to generate a predicted output, e.g., signal patterns associated with particular types of brainwave data in which the effects of such signal patterns are reduced or removed from the brainwave data.

In some implementations, instructions or code for implementing the one or more neural networks 114 can be stored in storage 108 and executable by processor 102. In some implementations, the one or more neural networks 114 can be implemented as a combination of hardware and software, and can provide or receive data to or from the processor 102. For instance, the processor 102 can provide training data to the one or more neural networks 114. In some cases, the processor 102 can transmit brainwave data to the one or more neural networks 114. In response, the one or more neural networks 114 can provide data indicative of one or more artifacts or corrective steps corresponding to the brainwave data.

In some implementations, the one or more neural networks 114 can include a deep learning neural network. The deep learning neural network is a machine learning model that employs multiple layers of models to generate an output for a received input. The deep neural network is a deep machine learning model that includes an output layer and one or more hidden layers that each apply a non-linear transformation to a received input to generate an output. In some cases, the neural network can be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a shallow machine learning model, e.g., a linear regression model or a generalized linear model.

The machine learning model can be a feed forward auto encoder neural network. For example, the machine learning model can be a three-layer auto encoder neural network. The machine learning model can include an input layer, a hidden layer, and an output layer. In some implementations, the neural network has no recurrent connections between layers. Each layer of the neural network can be fully connected to the next, e.g., there may be no pruning between the layers. The neural network can include an ADAM optimizer for training the network and computing updated layer weights. In some implementations, the neural network can apply a mathematical transformation, e.g., convolution, to input data prior to feeding the input data to the network.

In some implementations, the machine learning model can be a supervised model. For example, for each input provided to the model during training, the machine learning model can be instructed as to what the correct output should be. The machine learning model can use batch training, e.g., training on a subset of examples before each adjustment, instead of the entire available set of examples. This may improve the efficiency of training the model and may improve the generalizability of the model. The machine learning model can use folded cross-validation. For example, some fraction (the "fold") of the data available for training can be left out of training and used in a later testing phase to confirm how well the model generalizes.

For example, a machine learning model can be trained to recognize signal patterns in brainwave data that include or exclude artifacts. The machine learning model can correlate identified participant noise, environmental noise, and/or cap noise with signal patterns within the brainwave data that are related to these artifacts.

In some implementations, the machine learning model can refine the ability to identify signal patterns associated with artifacts for a particular user. For example, the machine learning model can continue to be trained on user specific data in order to adapt the signal pattern recognition algorithms to those associated with a particular patient. For example, the machine learning model can use brainwave data from periods of time during which the patient does not perform any physiological actions, e.g., during periods of time when the patient is substantially motionless. The machine learning model can use such data to develop a baseline for the patient's brainwave data absent noise and interference signal from other (non-brain related) physiological activity. The machine learning model can compare such baseline brainwave data to brainwave data with noise/interference signals due to one or more other patient actions to more accurately identify the effects of the various different types of noise on the brainwave data.

In some implementations, the data processor 102 can include an artifact classifier 116. The artifact classifier 116 can be trained using the one or more neural networks 114 and machine. The artifact classifier 116 is configured to process the data obtained via the I/O systems 112 from brainwave sensor system 105 by executing one or more operations that include determining line noise signal to noise ratio, calculating mutual information between sensor pairs, and applying the p-welch method. These three techniques are described in more detail below with respect to FIG. 5. As a result of executing these techniques, the artifact classifier 116 can obtain an indication of whether or not the brainwave data obtained from brainwave sensor system 105 contains any artifacts. The artifact classifier 116 can then use the artifact indication and confidence thresholds associated with a particular type of artifact to determine whether the brainwave data includes the particular type of artifact.

Processor 102 can communicate with the storage 108 to obtain output messages that are mapped to a particular type of artifact. The output messages can then be output to a technician through I/O systems 112. For example, if the artifact classifier 116 determines that obtained brainwave data includes an artifact corresponding to participant noise, the processor 102 will obtain a message that corresponds to the participant noise template from storage 108. I/O systems 112 can then output the message is through any suitable medium, such as a display device and/or a speaker.

Figure 5:
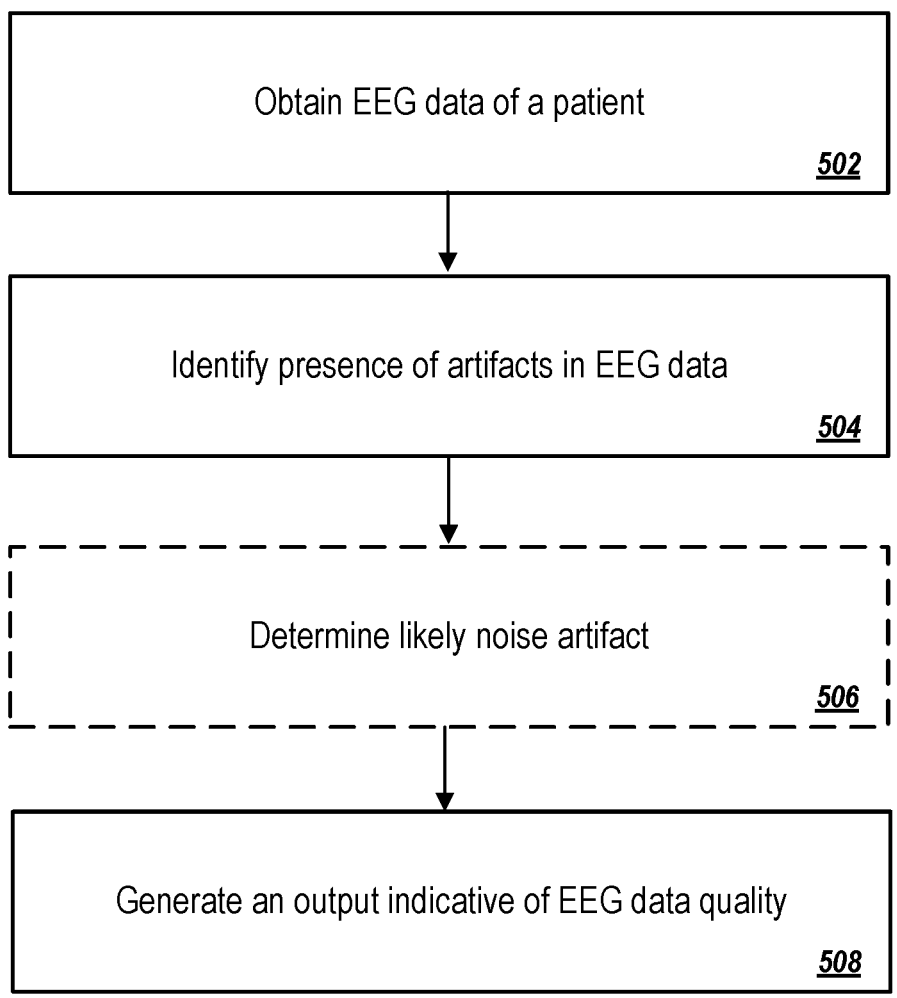
FIG. 5 depicts a flowchart of an example process for providing an indication of the presence of artifacts in brainwave data according to implementations of the present disclosure.

FIG. 5 depicts a flowchart of an example process for providing an indication of the presence of artifacts in brainwave or EEG data. In some implementations, the process 500 can be performed by one or more computer-executable programs executed using one or more computing devices. In some examples, the process 500 is executed by an EEG measurement system implemented at the data processor 102 of FIG. 1, or a computing device such as computing device 118 or wearable device 200.

The process 500 can be initiated by obtaining EEG data from one or more brainwave sensors (502). To do this, a wearable device, such as wearable device 200, is placed on a patient's head, as depicted and described with respect to FIG. 2. The wearable device is connected through a wired or wireless connection to a computing device, such as computing device 118. The computing device includes a data processor that obtains EEG data transmitted from the brainwave sensors.

EEG data can include data of a voltage signal indicative of the patient's brainwave activity over a particular period of time. This time period may be any suitable time period set by the technician.

EEG or brainwave activity data can include brainwaves that are related to the mental activity of a user, e.g., Alpha brainwaves, Gamma brainwaves, Beta brainwaves, Delta brainwaves, and Theta brainwaves. Alpha brainwaves are associated with lapses in attention and sleepiness. Gamma brainwaves are associated with cognitive activity, such as mental calculation. Beta brainwaves may be associated with alertness or anxious thinking. Delta brainwaves are characteristic of slow wave sleep. Theta brainwave phase may be associated with the commission of a cognitive error and theta activity is greater during high levels of alertness to auditory stimulation.

As described above, EEG data can include aggregated electrical signals that represent signal patterns related to the mental activity of the patient that may or may not have been compromised by patient noise, environmental noise, and/or cap noise. For example, user muscular movements (e.g., in the face, head, and eyes), heartbeats, and respiration create noise in the brainwave signals received by brainwave sensors 104. The noise can also be due to other electrical signals in the body (e.g., nervous system impulses to control muscle movements), other brain signals for controlling such movements, or both. A signal pattern related to physical movements of the user may be interpreted as noise with respect to the signal pattern related to the mental activity of the user, or vice versa depending on which signal pattern is desired for analysis.

In addition to patient noise, cap noise can be generated when one or more sensors in a wearable device or EEG cap have poor contact with a patient's scalp or are not operating properly. Environmental noise can be generated as a result of electromagnetic interferences that exist in the environment such as a cell phone signal or electrical humming resulting from a high powered electromagnetic device being operated within a certain distance of the patient. Line noise generated as a result of electrical appliances such as microwaves or refrigerators being plugged into a socket can also contribute to environmental noise.

The obtained EEG data can be preprocessed for subsequent data processing. In general, various suitable types of preprocessing can be implemented. For example, the EEG data can be filtered, downsampled, and/or converted to frequency domain data using techniques such as Fast Fourier Transform or a Welch periodogram. The obtained EEG data can be separated such that EEG data in response to specific events can be processed and stored. In some cases, the EEG data from multiple brainwave sensors can be aggregated and processed.

After obtaining and optionally preprocessing the EEG data, the data processor executes one or more methods to identify a presence of artifacts in the EEG data (504). Artifacts in EEG data can be identified using several techniques including line noise signal-to-noise ratio (SNR), mutual sensor pair information, the p-welch method, or a combination thereof.

Line Noise SNR

Figure 6A:
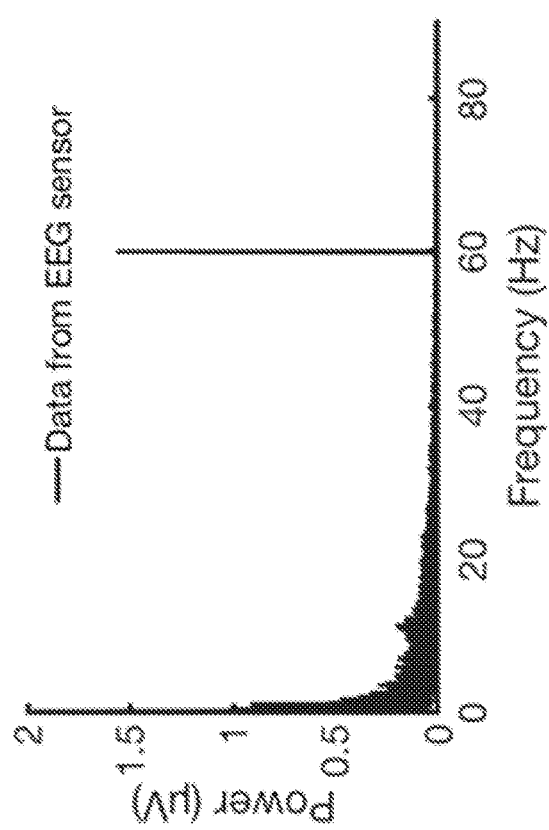
FIG. 6A depicts a power spectrum of EEG data according to implementations of the present disclosure.

As noted above, EEG data obtained from the brainwave sensors can be converted from time domain to frequency domain. A power spectrum of the frequency domain data can then be generated. Electrical noise of the EEG data can be recognized by determining the signal to noise ratio across the power spectrum. A spike or peak in the SNR at a frequency associated with one or more of a utility line frequency, power line frequency, and an alternating current frequency, e.g., 60 Hz in a local power line in the US, is generally indicative of excessive electrical noise or interference in the environment, which can be mediated by minimizing the noise from nearby electrical devices. An example of such a 60 Hz spike is illustrated in FIG. 6A. Thus, if the SNR of EEG data obtained from a sensor has a 60 Hz peak, as shown in FIG. 6A, the obtained EEG is likely affected by environmental or electrical noise.

In more detail, conversion of the EEG data to frequency domain data can be achieved by using Fast Fourier Transform (FFT), Discrete Fourier Transform (DFT), the p-Welch method, or other conversion methods. From the raw frequency domain data, a power spectrum of the SNR derived from the EEG data can be generated. In some cases, a bandpass filter can be applied to narrow the analysis of the power spectrum to a region with a center frequency of 60 Hz, e.g., a region of 50 Hz to 70 Hz.

A peak detection algorithm can be used to determine whether a peak exists at 60 Hz, or more generally with a frequency associated with one or more of a utility line frequency, power line frequency, and an alternating current frequency. For example, in some cases, a comparator can be used to determine if the SNR at 60 Hz is greater than or less than a particular SNR threshold. If the signal power is greater than or equal to the particular SNR threshold, the data processor determines that a SNR peak exists at 60 Hz and generates an output signal indicating the likely presence of a 60 Hz line noise artifact. If the SNR value at 60 Hz is less than the particular SNR threshold, the data processor determines that significant line noise to interfere with good quality EEG data does not exist, and generates an output signal indicating that the EEG data is likely not affected by 60 Hz line noise. The SNR threshold can be set or adjusted by the technician or author of the algorithm. The data processor can execute the peak detection algorithm, e.g., code for implementing the compactor to detect a 60 Hz peak.

Mutual Sensor Pair Information

The data processor can also determine mutual information between two sensors to determine the presence of an artifact due to cap noise. In particular, if each electrode in a wearable device is treated as a random variable, true biological data would have a moderate amount of shared dependence between those variables. Mutual information can be determined for any two sensors in the wearable device, and is a measure of uncertainty. The mutual information between the two sensors can be determined by Equation (1) below.

$$I(X;Y) = \sum_{y \in \mathcal{Y}} \sum_{x \in X} p(x,y) \log\left(\frac{p(x,y)}{p(x)p(y)}\right). \tag{1}$$

In Equation (1), p(x) refers to the marginal probability distribution function associated with a first sensor, p(y) refers to the marginal probability distribution function associated with a second sensor, and p(x, y) refers to the joint probability function associated with the sensor pair including the first and second sensors.

In general, the higher the value of the mutual information, the larger the uncertainty. Thus, a value closer to one indicates a greater likelihood of the presence of an artifact present across all EEG sensors, such as electrical bridging of nearby sensor pairs. In general, if the mutual information is greater than or equal to a particular threshold value, the system can determine that an artifact is present in the EEG data. The particular threshold value can be set by the technician or manufacturer of the wearable device.

In more detail, when a wearable device is connected to the data processor, the data processor may identify each sensor in the wearable device and maintain separate records for each sensor. For example, EEG data obtained from each sensor may be stored in different memory locations. Accordingly, EEG data can be obtained and correlated to specific sensors.

The data processor can then determine the various combinations of sensor pairs in the wearable device and determine the mutual information for one or more of the sensor pairs in the wearable device. In some cases, if the mutual information is greater than or equal to a particular mutual information threshold value, the data processor determines that an artifact is present in the EEG data and generates an output signal indicating the likely presence of a cap noise artifact. If the mutual information is less than the particular mutual information threshold value, the data processor determines that an artifact is not present in the EEG data and generates an output signal indicating that a cap noise artifact likely is not present.

P-Welch Method

Figure 6B:
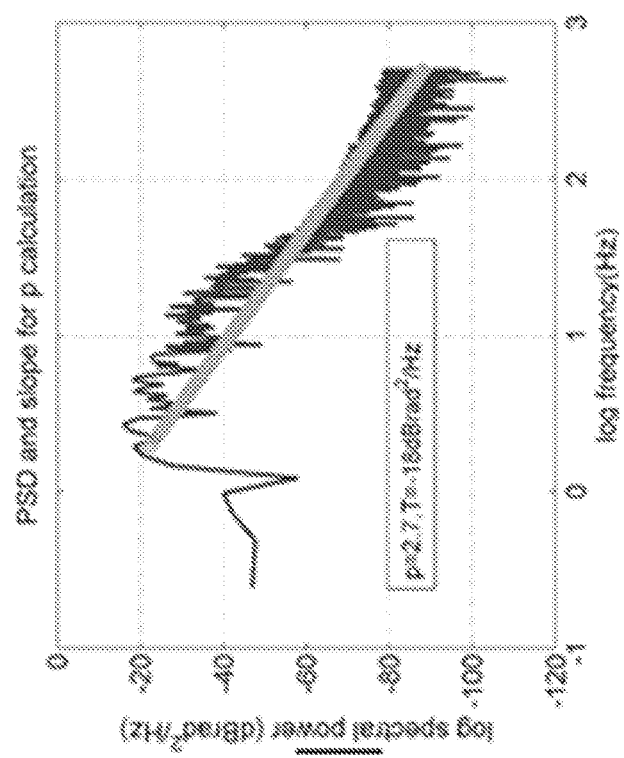
FIG. 6B depicts a slope fitted to the logged power spectrum of EEG data according to implementations of the present disclosure.

Like the SNR method, in the P-welch method, EEG data obtained from the brainwave sensors can be converted from time domain to frequency domain. A power spectrum of the frequency domain data is generated and logged. Next, a first degree polynomial is fitted to the logged power spectrum and a slope of the polynomial is determined, as shown in FIG. 6B.

In general, when EEG data contains no artifacts, the logged power spectrum has a shape consistent with a 1/f spectral distribution pattern. Thus, if the slope is a poor fit to the 1/f spectral distribution pattern, the EEG data likely contains artifacts. Furthermore, the shape of the power spectrum data can also provide insight into the type of noise. For instance, white noise is a random signal having equal intensity at different frequencies, giving it a constant power spectral density, and would result in a flat frequency distribution, indicating an error. More broadly, any non 1/f frequency distribution is suggestive of some sort of abnormality in the data.

In some implementations, after applying one or more of the line noise signal-to-noise ratio (SNR), mutual sensor pair information, and the p-welch method (collectively referred to as "artifacts tests") to the EEG data, a likely noise artifact can be determined by comparing the results of the artifacts tests to models that have been generated using an artifact classifier as described above (506).

For example, a peak detected at 60 Hz when determining Line Noise SNR may generally indicate the presence of electrical interference with the brainwave or EEG measurements. However, additional models can be used to supplement this analysis to determine the particular type of electrical interference. For instance, power spectrum envelopes or the amplitude values of the 60 Hz peak may correspond to particular types of noise.

As an example, a model for cell phone interference may indicate a particular range of amplitude values at higher frequencies (e.g., 700 MHz to 2.5 GHz) that is different from the range of amplitude values for the 60 Hz peak in a model for line-based interference arising from, e.g., when a microwave or refrigerator near the patient is turned on. Additionally, the power spectrum envelope associated with EEG data affected by cell phone interference may be different from a power spectrum envelope associated with EEG data affected by line-based interference.

By comparing the power spectrum envelope and/or amplitude values at 60 Hz of the obtained EEG data to these models, the EEG measurement system can determine the likely noise artifact in an EEG measurement. In the current example, the EEG measurement system can determine that EEG data includes an environmental artifact that is, e.g., likely a line-based artifact if the 60 Hz amplitude values and/or power spectrum envelop of the EEG data corresponds to the 60 Hz amplitude values and/or power spectrum envelop in a line noise model.

For the p-welch method, certain slopes may be associated with a particular type of artifact. Thus, if the slope of obtained EEG data corresponds to a slope in a model for a particular artifact, the EEG measurement system can determine that the obtained EEG data likely is affected by noise associated with the particular type of artifact.

For Mutual Sensor Pair Information artifact tests, certain values of the mutual information I(X,Y) may indicate the likely presence of a particular type of artifact. For example, a particular range of values can indicate that one of the sensors does not have good contact with a patient's scalp. A second range of values can indicate that both sensors do not have good contact with a patient's scalp.

In general, various types of models can be used in conjunction with the artifact tests to determine the presence of an artifact in brainwave or EEG data, and, in some cases, a particular type of artifact present in the brainwave or EEG data.

In some implementations, when comparing the results of the artifacts tests to models that have been generated using training data and neural networks, a similarity threshold can be used. A result of an artifact tests is determined to be similar to a model if the similarity between the result of the artifact test and the model is greater than or equal to the similarity threshold.

After the determination is made, the EEG measurement system can generate an output indicative of a quality of the obtained EEG data (508). For example, in some cases, a binary output system can be used in which a first signal is generated if the obtained EEG data likely does not contain any artifacts, and a second signal is generated if the obtained EEG data likely does contain artifacts. These first and second signal can be implemented in various formats such as light signals, audio signals, or other representative forms. For instance, a green light can be output if the obtained EEG data likely does not contain any artifacts. A red light can be output if the EEG data likely does contain an artifact.

In some cases, an audio message such as "[T]his EEG measurement does not contain any artifacts" can be output if the obtained EEG data likely does not contain any artifacts. An audio message such as "[T]his EEG measurement contains at least one artifact" can be output if the EEG data likely does contain an artifact. In general, various suitable types of signals and indicators can be used to indicate the presence or lack of indicators in obtained EEG data.

In some implementations, if a particular type of artifact is determined to be likely present, the EEG measurement system can output a message associated with the particular type of artifact. In particular, if the EEG measurement system determines that obtained EEG data likely contains a particular type of artifact, the EEG measurement system can transmit a request to the mapping table described above for an output message template associated with particular type of artifact. After receiving the request, the mapping table can look up the output message template associated with the particular type of artifact, and can transmit the output message template to the EEG measurement system. After receiving the output message template from the mapping table, the EEG measurement system can generate an output using the output message template. The output can be generated in various formats and using any suitable method.

As another example, if the EEG measurement system determines that obtained EEG data likely includes an artifact due to the patient grinding teeth, the EEG measurement system can transmit a request for an output message template associated with a patient grinding teeth to the mapping table. After receiving the output message template from the mapping table, the EEG measurement system can then output a message to the technician or patient indicating that the obtained EEG data includes participant noise. In some cases, the output template may include a recommendation for minimizing participant noise. For example, the EEG measurement system can generate a message such as "Please request the patient to stop grinding teeth."

In another example, when a mutual sensor pair information test is performed and data from a particular pair of sensors is determined to likely include a cap noise artifact, the EEG measurement system can transmit a request for an output message template associated with a cap noise error. The template can include a field for an identification of each of the sensors (e.g., sensors A and B) in the sensor pair being tested. After receiving the output message template from the mapping table, the EEG measurement system can generate a message such as "Please double check the contact between the patient and sensors A and B."

Figure 7:
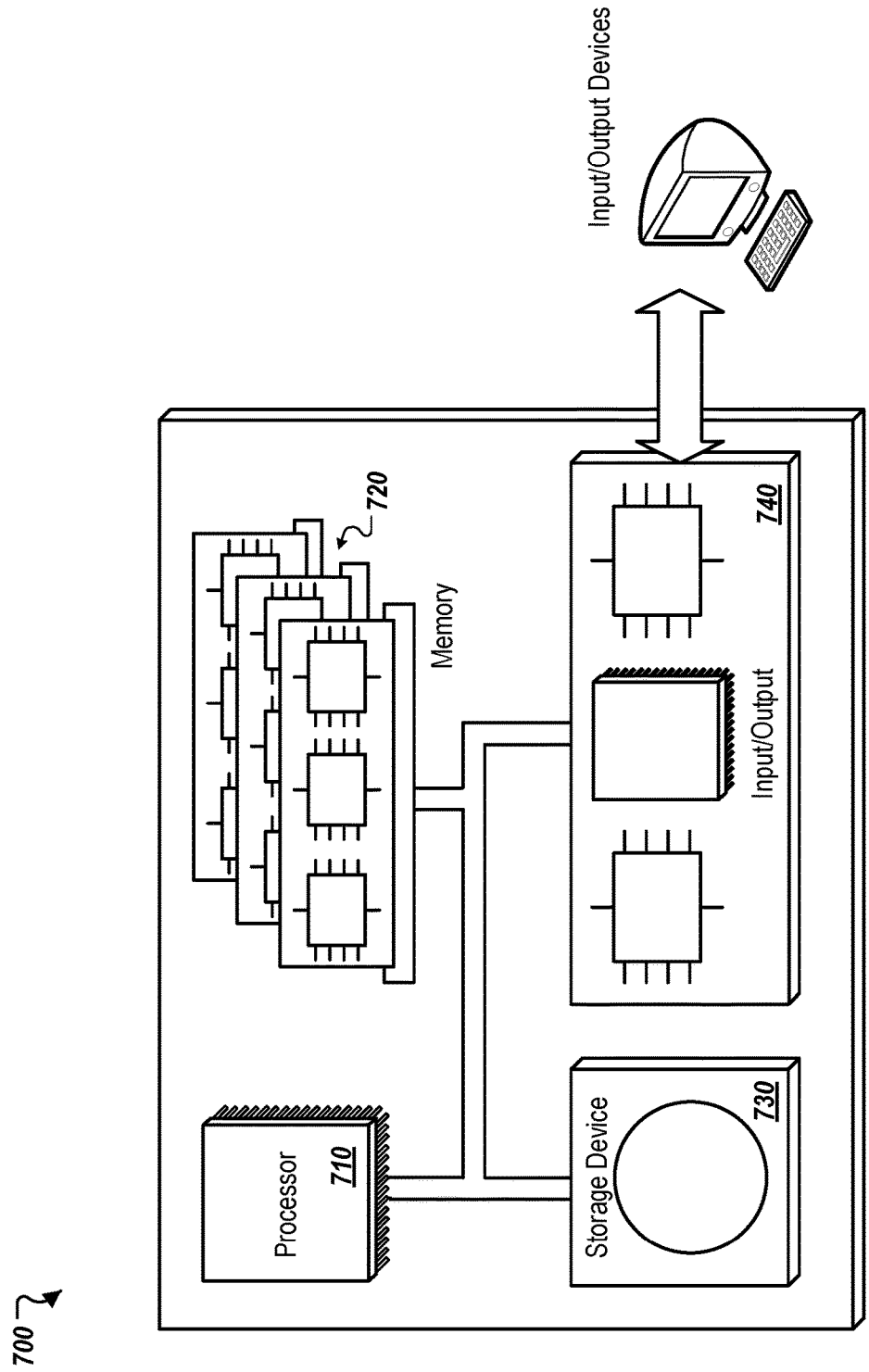
FIG. 7 depicts a schematic diagram of a computer system that can be applied to any of the computer-implemented methods and other techniques described herein.

FIG. 7 is a schematic diagram of a computer system 700. The system 700 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 700) and their structural equivalents, or in combinations of one or more of them. The system 700 is intended to include various forms of digital computers, such as laptops, desktops, workstations, personal digital assistants, servers, blade servers, mainframes, and other appropriate computers, including vehicles installed on base units or pod units of modular vehicles. The system 700 can also include mobile devices, such as personal digital assistants, cellular telephones, smartphones, and other similar computing devices. Additionally, the system can include portable storage media, such as, Universal Serial Bus (USB) flash drives. For example, the USB flash drives can store operating systems and other applications. The USB flash drives can include input/output components, such as a wireless transducer or USB connector that can be inserted into a USB port of another computing device.

The system 700 includes a processor 710, a memory 720, a storage device 730, and an input/output device 740. Each of the components 710, 720, 730, and 740 are interconnected using a system bus 550. The processor 710 is capable of processing instructions for execution within the system 700. The processor can be designed using any of a number of architectures. For example, the processor 710 may be a CISC (Complex Instruction Set Computers) processor, a RISC (Reduced Instruction Set Computer) processor, or a MISC (Minimal Instruction Set Computer) processor.

In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 can include or be coupled to a keyboard and/or pointing device. In another implementation, the input/output device 740 can include or be coupled to a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a technician or patient, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

It should be understood that the phrase one or more of and the phrase at least one of include any combination of elements. For example, the phrase one or more of A and B includes A, B, or both A and B. Similarly, the phrase at least one of A and B includes A, B, or both A and B.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

What is claimed is:

1. A computer-implemented method executed by one or more processors and comprising:
    obtaining brainwave data from a wearable device comprising brainwave sensors;
    determining that an artifact is likely present in the brainwave data by performing an artifact detection process comprising a P-welch method, wherein performing the P-welch method comprises:
        generating frequency brainwave data from the brainwave data obtained from the brainwave sensors;
        generating a power spectrum of the frequency brainwave data;
        applying a first degree polynomial to a logged representation of the power spectrum; and
        determining that a slope of the first degree polynomial or shape of the logged representation of the power spectrum corresponds to a slope or shape associated with an artifact;
    obtaining an output message template corresponding to the artifact that is likely present in the brainwave data; and
    generating an output indicative of a quality of the brainwave data based on the output message template corresponding to the artifact that is likely present in the brainwave data.

2. The computer-implemented method of claim 1, wherein determining that an artifact is likely present in the brainwave data by performing an artifact detection process further comprises performing a line noise signal to noise ratio (SNR)-based determination comprising:
    determining a signal to noise ratio across the power spectrum; and
    determining a signal to noise ratio peak at a predetermined frequency associated with one or more of a utility line frequency, power line frequency, and an alternating current frequency.

3. The computer-implemented method of claim 1, wherein determining that an artifact is likely present in the brainwave data by performing an artifact detection process further comprises performing a mutual information determination comprising:
    determining a mutual information value between two sensors of the brainwave sensors; and
    determining that the mutual information value is greater than or equal to a threshold value.

4. The computer-implemented method of claim 1, wherein determining that an artifact is likely present in the brainwave data comprises performing two or more of a line noise signal to noise ratio (SNR)-based determination, a mutual information-based determination, and the P-welch method.

5. The computer-implemented method of claim 1, further comprising identifying, based on one or more features of the artifact, a type of the artifact as one or more of a participant-based artifact, environmental artifact, and a cap-based artifact in the brainwave data in response to determining that an artifact is likely present in the brainwave data.

6. The computer-implemented method of claim 5, wherein identifying the type of the artifact data as one or more of a participant-based artifact, environmental artifact, and a cap-based artifact comprises:
    obtaining artifact models from an artifact database;
    comparing the one or more features of the artifact to the artifact models;

determining that a similarity between the one or more features of the artifact and one of the artifact models satisfies a similarity threshold; and determining that the brainwave data includes one or more of a participant-based artifact, environmental artifact, and a cap-based artifact in response to determining that the similarity threshold is satisfied.

7. The computer-implemented method of claim 6, wherein the artifact models are generated using a neural network and training data.

8. The computer-implemented method of claim 5, wherein obtaining the output message template corresponding to the artifact that is likely present in the brainwave data comprises:

transmitting, to a mapping table database, a request for an output message template corresponding to the one or more of a participant-based artifact, environmental artifact, and a cap-based artifact identified in the brainwave data; and receiving, from the mapping table database, the output message template.

9. The computer-implemented method of claim 1, wherein the output message template includes one or more instructions that direct an EEG technician to perform particular actions for reducing or eliminating the artifact.

10. A system comprising:

a wearable device comprising brainwave sensors configured to obtain brainwave data; and a data processor communicably coupled to the brainwave sensors, the data processor being configured to:

determine that an artifact is likely present in the brainwave data by performing an artifact detection process comprising a p-welch method, wherein performing the p-welch method comprises:

generating frequency brainwave data from the brainwave data obtained from the brainwave sensors;

generating a power spectrum of the frequency brainwave data;

applying a first degree polynomial to a logged representation of the power spectrum; and determining that a slope of the first degree polynomial or shape of the logged representation of the power spectrum corresponds to a slope or shape associated with an artifact;

obtain an output message template corresponding to the artifact that is likely present in the brainwave data; and generate an output indicative of a quality of the brainwave data based on the output message template corresponding to the artifact that is likely present in the brainwave data.

11. The system of claim 10, wherein the data processor being configured to determine that an artifact is likely present in the brainwave data comprises the data processor being configured to perform two or more of a line noise signal to noise ratio (SNR)-based determination, a mutual information-based determination, and the P-welch method.

12. The system of claim 10, wherein the data processor is further configured to identify the artifact as one or more of a participant-based artifact, environmental artifact, and a cap-based artifact in the brainwave data in response to determining that an artifact is likely present in the brainwave data.

13. The system of claim 12, wherein the data processor being configured to identify one or more of a participant-based artifact, environmental artifact, and a cap-based artifact comprises the data processor being configured to:

obtain artifact models from an artifact database;

compare one or more features of the artifact to the artifact models;

determine that a similarity between the one or more features of the artifact and one of the artifact models satisfies a similarity threshold; and determine that the brainwave data includes one or more of a participant-based artifact, environmental artifact, and a cap-based artifact in response to determining that the similarity threshold is satisfied.

14. The system of claim 12, wherein the data processor being configured to obtain the output message template corresponding to the artifact that is likely present in the brainwave data comprises the data processor being configured to:

transmit, to a mapping table database, a request for an output message template corresponding to the one or more of a participant-based artifact, environmental artifact, and a cap-based artifact identified in the brainwave data; and receive, from the mapping table database, the output message template.

15. A non-transitory computer-readable storage medium comprising instructions, which when executed by one or more computers, cause the one or more computers to execute operations comprising:

obtaining brainwave data from a wearable device comprising brainwave sensors;

determining that an artifact is likely present in the brainwave data by performing an artifact detection process comprising a p-welch method, wherein performing the P-welch method comprises:

generating frequency brainwave data from the brainwave data obtained from the brainwave sensors;

generating a power spectrum of the frequency brainwave data;

applying a first degree polynomial to a logged representation of the power spectrum; and determining that a slope of the first degree polynomial or shape of the logged representation of the power spectrum corresponds to a slope or shape associated with an artifact;

obtaining an output message template corresponding to the artifact that is likely present in the brainwave data; and generating an output indicative of a quality of the brainwave data based on the output message template corresponding to the artifact that that is likely present in the brainwave data.

16. The non-transitory computer-readable storage medium of claim 15, wherein determining that an artifact is likely present in the brainwave data comprises performing two or more of a line noise signal to noise ratio (SNR)-based determination, a mutual information-based determination, and the P-welch method.

17. The non-transitory computer-readable storage medium of claim 15, further comprising:

identifying, based on one or more features of the artifact, a type of the artifact as one or more of a participant-based artifact, environmental artifact, and a cap-based artifact in the brainwave data in response to determining that an artifact is likely present in the brainwave data.

18. The non-transitory computer-readable storage medium of claim 17, wherein identifying type of the artifact as one or more of a participant-based artifact, environmental artifact, and a cap-based artifact comprises:

obtaining artifact models from an artifact database;
comparing the one or more features of the artifact to the artifact models;
determining that a similarity between the one or more features of the artifact and one of the artifact models satisfies a similarity threshold; and
determining that the brainwave data includes one or more of a participant-based artifact, environmental artifact, and a cap-based artifact in response to determining that the similarity threshold is satisfied.

19. The non-transitory computer-readable storage medium of claim 17, wherein obtaining the output message template corresponding to the artifact that is likely present in the brainwave data comprises:
transmitting, to a mapping table database, a request for an output message template corresponding to the one or more of a participant-based artifact, environmental artifact, and a cap-based artifact identified in the brainwave data; and
receiving, from the mapping table database, the output message template.

20. A computer-implemented method executed by one or more processors and comprising:
obtaining brainwave data from a wearable device comprising brainwave sensors;
determining that an artifact is likely present in the brainwave data and identifying one or more features of the artifact by performing an artifact detection process comprising one or more of a line noise signal to noise ratio (SNR)-based determination, a mutual information-based determination, and a P-welch method;
identifying a type of the artifact by:
obtaining artifact models from an artifact database;
comparing the one or more features of the artifact to the artifact models;
determining that a similarity between the one or more features of the artifact and one of the artifact models satisfies a similarity threshold; and
determining that the brainwave data includes one or more of a participant-based artifact, environmental artifact, and a cap-based artifact in response to determining that the similarity threshold is satisfied;
obtaining an output message template corresponding to the type of the artifact that is likely present in the brainwave data; and
generating an output indicative of a quality of the brainwave data based on the output message template corresponding to the type of the artifact that is likely present in the brainwave data.

21. A system comprising:
a wearable device comprising brainwave sensors configured to obtain brainwave data; and
a data processor communicably coupled to the brainwave sensors, the data processor being configured to:
determine that an artifact is likely present in the brainwave data and identify one or more features of the artifact by performing an artifact detection process comprising one or more of a line noise signal to noise ratio (SNR)-based determination, a mutual information-based determination, and a p-welch method;
identify a type of the artifact by:
obtaining artifact models from an artifact database;
comparing the one or more features of the artifact to the artifact models;
determining that a similarity between the one or more features of the artifact and one of the artifact models satisfies a similarity threshold; and
determining that the brainwave data includes one or more of a participant-based artifact, environmental artifact, and a cap-based artifact in response to determining that the similarity threshold is satisfied;
obtain an output message template corresponding to the type of the artifact that is likely present in the brainwave data; and
generate an output indicative of a quality of the brainwave data based on the output message template corresponding to the type of the artifact that is likely present in the brainwave data.

22. A non-transitory computer-readable storage medium comprising instructions, which when executed by one or more computers, cause the one or more computers to execute operations comprising:
obtaining brainwave data from a wearable device comprising brainwave sensors;
determining that an artifact is likely present in the brainwave data and identifying one or more features of the artifact by performing an artifact detection process comprising one or more of a line noise signal to noise ratio (SNR)-based determination, a mutual information-based determination, and a P-welch method;
identifying a type of the artifact by:
obtaining artifact models from an artifact database;
comparing the one or more features of the artifact to the artifact models;
determining that a similarity between the one or more features of the artifact and one of the artifact models satisfies a similarity threshold; and
determining that the brainwave data includes one or more of a participant-based artifact, environmental artifact, and a cap-based artifact in response to determining that the similarity threshold is satisfied;
obtaining an output message template corresponding to the type of the artifact that is likely present in the brainwave data; and
generating an output indicative of a quality of the brainwave data based on the output message template corresponding to the type of the artifact that is likely present in the brainwave data.

* * * * *